United States Patent
Couvineau et al.

(10) Patent No.: US 10,172,921 B2
(45) Date of Patent: Jan. 8, 2019

(54) METHOD OF TREATING AN INFLAMMATORY BOWEL DISEASE COMPRISING AGONISTS OF OREXIN-1 RECEPTOR

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); ASSISTANCE PUBLIQUE—HÔPITAUX DE PARIS, Paris (FR)

(72) Inventors: Alain Couvineau, Paris (FR); Thierry Voisin, Paris (FR); Nassima Messal, Paris (FR); Eric Ogier-Denis, Paris (FR); Xavier Treton, Paris (FR)

(73) Assignees: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); ASSISTANCE PUBLIQUE—HÔPITAUX DE PARIS, Paris (FR)

( * ) Notice: Subject to any disclaimer, the term of this patent is extended or adjusted under 35 U.S.C. 154(b) by 0 days.

(21) Appl. No.: 15/320,827

(22) PCT Filed: Jun. 23, 2015

(86) PCT No.: PCT/EP2015/064028
§ 371 (c)(1),
(2) Date: Dec. 21, 2016

(87) PCT Pub. No.: WO2015/197572
PCT Pub. Date: Dec. 30, 2015

(65) Prior Publication Data
US 2017/0202925 A1    Jul. 20, 2017

(30) Foreign Application Priority Data

Jun. 24, 2014 (EP) .................................... 14305990

(51) Int. Cl.
*A61K 38/00* (2006.01)
*A61K 38/22* (2006.01)
*A61K 45/06* (2006.01)

(52) U.S. Cl.
CPC .............. *A61K 38/22* (2013.01); *A61K 45/06* (2013.01)

(58) Field of Classification Search
CPC ...................................................... A61K 38/22
See application file for complete search history.

(56) References Cited

U.S. PATENT DOCUMENTS

2006/0177444 A1* 8/2006 Horizoe ................. A61K 31/00
424/145.1
2010/0204110 A1* 8/2010 Bevec .................... A61K 38/12
514/5.5

FOREIGN PATENT DOCUMENTS

WO        01/00787 A2    1/2001

OTHER PUBLICATIONS

Darkers et al., Bioorganic & Med. Chem. Letters.11:737-740, 2001.*
Szlachcic et al, "Involvement of Orexigenic Peptides in the Mechanism of Gastric Mucosal Integrity and Healing of Chronic Gastric Ulcers", Current Pharmaceutical Design, Apr. 1, 2010, pp. 1214-1223, vol. 16, No. 10.
Chiou et al., "Orexins/Hypocretins: Pain Regulation and Cellular Actions", Sep. 1, 2010, pp. 3089-3100, vol. 16, No. 28.

* cited by examiner

*Primary Examiner* — Gyan Chandra
(74) *Attorney, Agent, or Firm* — Whitham & Cook, P.C.

(57) ABSTRACT

The present invention relates to methods and pharmaceutical compositions for the treatment of inflammatory bowel diseases. The presents methods relates to a method of treating an inflammatory bowel disease in a subject in need thereof comprising administering the subject with a therapeutically effective amount of at least one OX1R agonist.

11 Claims, 5 Drawing Sheets
Specification includes a Sequence Listing.

METHOD OF TREATING AN INFLAMMATORY BOWEL DISEASE COMPRISING AGONISTS OF OREXIN-1 RECEPTOR

FIELD OF THE INVENTION

The present invention relates to methods and pharmaceutical compositions for the treatment of inflammatory bowel diseases.

BACKGROUND OF THE INVENTION

Inflammatory bowel disease (IBD), including Crohn's disease (CD) and UC affects approximately 1.5 million Europeans, and its peak onset is in persons with 15 to 30 years of age. IBD incidence is still increasing in developing countries. In France, 64,399 UC patients were estimated from 2008 health security agency records. UC involves the rectum and may affect part of the colon or the entire colon (pancolitis) in an uninterrupted pattern. Changes in diet, antibiotic use, environmental risk factors, and intestinal microflora are involved in IBD pathogenesis and have contributed to the increased prevalence of IBD during the past century.

Despite tremendous advances in our understanding of the pathobiology of IBD, current treatments are not efficient to control the disease over the long term. Indeed, 15-25% of patients with UC are still operated on (total colectomy) and the most powerful treatments (anti-TNF antibodies) provide complete remission at one year of treatment in only 30% of the patients enrolled in clinical trials. Moreover, UC increases the risk of colorectal cancer (18% at 30 years). Recently, the estimated annual per-patient direct medical costs of UC ranged from $6217 to $11 477 in the USA and from € 8949 to € 10 395 in Europe. Hospitalizations accounted for 41-55% of direct medical costs. The indirect costs accounted for approximately one-third of total costs in the United States and 54-68% in Europe. The total economic burden of UC was estimated at $8.1-14.9 billion annually in the USA and at € 12.5-29.1 billion in Europe. Total direct costs were $3.4-8.6 billion in the USA and € 5.4-12.6 billion in Europe. Direct costs, hospitalizations and surgeries increased with worsening disease severity. UC is a costly disease and hospitalizations contribute significantly to direct medical costs, and indirect costs are considerable. A better medical control of the disease is required. So far, current treatments are empirically used in UC. They mainly target the immune system and inflammation (aminosalicylates, steroids, and immunomodulators), while new treatments targeting epithelial abnormalities (i.e. ER stress, oxidative stress) will probably be more effective (and better tolerated), to maintain a prolonged remission or even to cure UC. Thus, drugs that prevent primary epithelial defects are mandatory to better manage UC, improve patient's quality of life, avoid terminal complications and considerably reduce the costs of care of UC.

Orexins (orexin-A and orexin-B) are hypothalamic peptides involved in the sleep/wake control which interact with two class A GPCR sub-types, OX1R and OX2R. Activation of these receptors by orexins classically induced cellular calcium transients through Gq-dependant and -independent pathways. It was recently demonstrated that OX1R was highly ectopically expressed in digestive cancer cell lines derived from colon, pancreas and liver cancers in which orexins: 1) induce a strong mitochondrial apoptosis; 2) induce a strong inhibition of tumor growth in nude mice xenografted with cancer cells. These effects were mediated by an original mechanism involving: i) the presence of two ITIM (immunoreceptor tyrosine inhibitory motif) sequences in OX1R which are tyrosine phosphorylated in the presence of orexins; ii) the recruitment and activation of the tyrosine phosphatase SHP-2 which is responsible for mitochondrial apoptosis involving cytochrome c release from mitochondria to cytosol and caspase-3 and caspase-7 activation. However the involvement of orexins in the treatment of IBD has never been investigated.

SUMMARY OF THE INVENTION

The present invention relates to methods and pharmaceutical compositions for the treatment of inflammatory bowel diseases.

DETAILED DESCRIPTION OF THE INVENTION

The inventors demonstrate that that OX1R was detected in human epithelia of Inflammatory Bowel Disease (IBD) including Crohn's disease and Ulcerative Colitis (UC). Based on these observations, they have investigated the effect of Orexin A (OxA) on acute inflammation in mice treated with Dextran Sulfate Sodium (DSS) and show that the OxA treatment of DSS-treated mice ameliorates the Disease Activity Index (DAI) and also histologic aspect of colon epithelium. Moreover, OxA reduces the secretion of "pro-inflammatory" cytokines such as TNFα, IL6, IL8 homolog and IL1B in colon extracts of DSS-induced colitis mice. The recent development of a new spontaneous UC-like mouse model (EXCY2 mice, WO/2012/140516) is ideally suited to study the OxA effect on spontaneous colitis. The inventors reveal that OxA treatment protected severe colitis in 10 week-old EXCY2 mice. Indeed, OxA-treated EXCY2 mice exhibited a normal colonic mucosa as compared to vehicle treated EXCY2 mice. Furthermore, the system OxA/OX1R induced two main deregulated pathways involved in the onset of colitis, i.e. oxidative stress and ER stress, in both EXCY2 mice and Caco2 cells. These results indicate that the OX1R agonists are suitable for the treatment of inflammatory bowel disease.

Accordingly an object of the present invention relates to a method of treating an inflammatory bowel disease in a subject in need thereof comprising administering the subject with a therapeutically effective amount of at least one OX1R agonist.

As used herein, the term "subject" denotes a mammal, such as a rodent, a feline, a canine, and a primate. Preferably, a subject according to the invention is a human.

As used herein the term "inflammatory bowel disease" has its general meaning in the art and refers to any inflammatory disease that affects the bowel. The term includes but is not limited to ulcerative colitis, Crohn's disease, especially Crohn's disease in a state that affect specifically the colon with or without ileitis, microscopic colitis (lymphocytic colitis and collagenous colitis), infectious colitis caused by bacteria or by virus, radiation colitis, ischemic colitis, pediatric colitis, undetermined colitis, and functional bowel disorders (described symptoms without evident anatomical abnormalities). In some embodiments, the method of the invention is particularly suitable for the treatment of ulcerative colitis.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The tem "treatment" encompasses the prophylactic treatment. As used herein, the term "prevent" refers to the reduction in the risk of acquiring or developing a given condition, or the reduction or inhibition of the recurrence or said condition in a subject who is not ill, but who has been or may be near a subject with the disease.

As used herein, the tem "OX1R" has its general meaning in the art and refers to the 7-transmembrane spanning receptor OX1R for orexins. An exemplary amino acid sequence of OX1R is shown as SEQ ID NO:1.

In some embodiments, the OX1R agonist is a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more In particular up to 2000 Da, and most In particular up to about 1000 Da.

In some embodiment, the OX1R agonist is an OX1R antibody or a portion thereof.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

In one embodiment of the antibodies or portions thereof described herein, the antibody is a monoclonal antibody. In

```
SEQ ID NO: 1: human orexin receptor-1 OX1R
    1   mepsatpgaq mgvppgsrep spvppdyede flrylwrdyl ypkqyewvli aayvavfvva 61   lvgntlycla vwrnhhmrtv tnyfivnlsl advlvtaicl pasllvdite swlfghalck 121   vipylqaysv svavltlsfi aldrwyaich pllfkstarr argsilgiwa vslaimvpqa 181   avmecssvlp elanrtrlfs vcderwaddl ypkiyhscff ivtylaplgl mamayfqifr 241   klwgrqipgt tsalvrnwkr psdqlgdleq glsgepqprg raflaevkqm rarrktakml 301   mvvllvfalc ylpisvlnvl krvfgmfrqa sdreavyacf tfshwlvyan saanpiiynf 361   lsgkfreqfk aafscclpgl gpcgslkaps prssashksl slqsrcsisk isehvvltsv 421   ttvlp
```

Accordingly, as used herein, the term "OX1R agonist" refers to any compound natural or not that is able to bind to OX1R and promotes OX1R activity. In particular, an easy method for determining whether a compound is an OX1R agonist consists in determining whether the candidate is able to induce a transient calcium release in a cell expressing OX1R. In some other aspects a compound is OX1R agonist when is induces apoptosis of cancer cell lines expressing OX1R (e.g. colorectal cancer cell lines). Indeed OX1R promotes apoptosis in cancer cell lines through a mechanism which is not related to Gq-mediated phopholipase C activation and cellular calcium transients. Orexins induce indeed tyrosine phosphorylation of 2 tyrosine-based motifs in OX1R, ITIM and ITSM, resulting in the recruitment of the phosphotyrosine phosphatase SHP-2, the activation of which is responsible for mitochondrial apoptosis (Voisin T, El Firar A, Rouyer-Fessard C, Gratio V, Laburthe M. A hallmark of immunoreceptor, the tyrosine-based inhibitory motif ITIM, is present in the G protein-coupled receptor OX1R for orexins and drives apoptosis: a novel mechanism. FASEB J. 2008 June; 22(6):1993-2002; El Firar A, Voisin T, Rouyer-Fessard C, Ostuni M A, Couvineau A, Laburthe M. Discovery of a functional immunoreceptor tyrosine-based switch motif in a 7-transmembrane-spanning receptor: role in the orexin receptor OX1R-driven apoptosis. FASEB J. 2009 Dec.; 23(12):4069-80. doi: 10.1096/fj.09-131367. Epub 2009 Aug. 6.). of activation of signal transduction pathways involving recruitment of SHP-2 and the induction of apoptosis of the cell, independently of transient calcium release.

one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of OX1R. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Briefly, the recombinant OX1R may be provided by expression with recombinant cell lines. In particular, OX1R may be provided in the form of human cells expressing OX1R at their surface. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope. In both the heavy chain Fd fragment and the light chain of IgG immunoglobulins, there are four framework regions (FR1 through FR4) separated respectively by three complementarity determining regions (CDR1 through CDRS). The CDRs, and in particular the CDRS regions, and more particularly the heavy chain CDRS, are largely responsible for antibody specificity. It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In one embodiment of the agents described herein, the agent is a polypeptide. In a particular embodiment the polypeptide is a functional equivalent of Orexin-A or Orexin-B.

As used herein the term "Orexin-A" has its general meaning in the art and refers to the amino acid sequence as shown by SEQ ID NO:2.

Orexin-A: $_p$eplpdccrqk tcscrlyell hgagnhaagi ltlx (SEQ ID NO:2)

$_p$e means 2-pyrrolidone-5-carboxylic acid (Xaa: pyrrolidone carboxylic acid).

As used herein the term "orexin-B" has its general meaning in the art and refers to the amino acid sequence as shown by SEQ ID NO:3.

Orexin-B: fsgppglqgr lqrllqasgn haagiltm (SEQ ID NO:3) or glqgr lqrllqasgn haagiltm (SEQ ID NO:4).

As used herein, a "functional equivalent of orexin" is a polypeptide which is capable of binding to OX1R, thereby promoting an OX1R activity according to the invention. The term "functional equivalent" includes fragments, mutants, and muteins of Orexin-A and Orexin-B. The term "functionally equivalent" thus includes any equivalent of orexins (i.e. Orexin-A or Orexin-B) obtained by altering the amino acid sequence, for example by one or more amino acid deletions, substitutions or additions such that the protein analogue retains the ability to bind to OX1R and promote an OX1R activity according to the invention (e.g. aoptosis of the cancer cell). Amino acid substitutions may be made, for example, by point mutation of the DNA encoding the amino acid sequence.

In some embodiments, the functional equivalent is at least 70% of identity to the corresponding protein. According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence and conserving biological properties of said second amino acid sequence. Amino acid sequence identity is preferably determined using a suitable sequence alignment algorithm and default parameters, such as BLAST P (Karlin and Altschul, 1990).

The term "a functionally equivalent fragment" as used herein also may mean any fragment or assembly of fragments of Orexin that binds to OX1R and promote the OX1R activity according to the invention. Accordingly the present invention provides a polypeptide which comprises consecutive amino acids having a sequence which corresponds to the sequence of at least a portion of Orexin-A or Orexin-B, which portion binds to OX1R and promotes the OX1R activity according to the invention.

The polypeptides of the invention may be produced by any suitable means, as will be apparent to those of skill in the art. In order to produce sufficient amounts of polypeptides or functional equivalents thereof for use in accordance with the present invention, expression may conveniently be achieved by culturing under appropriate conditions recombinant host cells containing the polypeptide of the invention. In particular, the polypeptide is produced by recombinant means, by expression from an encoding nucleic acid molecule. Systems for cloning and expression of a polypeptide in a variety of different host cells are well known. When expressed in recombinant form, the polypeptide is in particular generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E. coli*.

In some embodiments, the polypeptide of the invention is an immunoadhesin.

As used herein, the term "immunoadhesin" designates antibody-like molecules which combine the binding specificity of a heterologous protein (an "adhesin" which is able to bind to OX1R) with the effector functions of immunoglobulin constant domains. Structurally, the immunoadhesins comprise a fusion of an amino acid sequence with the desired binding specificity to OX1R (i.e., is "heterologous"), and an immunoglobulin constant domain sequence. The adhesin part of an immunoadhesin molecule typically is a contiguous amino acid sequence comprising at least the binding site for OX1R. In one embodiment, the adhesin comprises the polypeptides characterized by SEQ ID NO:2, SEQ ID NO:3 or SEQ ID NO:4. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The immunoglobulin sequence typically, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

In one embodiment, the Fc region is a native sequence Fc region. In one embodiment, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The adhesion portion and the immunoglobulin sequence portion of the immunoadhesin may be linked by a minimal linker. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG3.

The polypeptides of the invention, fragments thereof and fusion proteins (e.g. immunoadhesin) according to the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In one embodiment, the OX1R agonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods.

The terms "administer" or "administration" refer to the act of injecting or otherwise physically delivering a substance as it exists outside the body (e.g., a OX1R agonist of the present invention) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

In some embodiments, the OX1R agonist of the invention is administered to the subject with a therapeutically effective amount.

By a "therapeutically effective amount" is meant a sufficient amount of OX1R to treat the inflammatory bowel disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the OX1R agonist of the present invention is administered to the subject in combination with a standard treatment. Typically the standard treatment is selected from the group consisting of corticosteroids, immunosuppressive drugs, aminosalicylates sulfasalazine, such as Mesalazine (also known as 5-aminosalicylic acid, mesalamine, or 5-ASA. Brand name formulations include Apriso, Asacol, Pentasa, Mezavant, Lialda, Fivasa, Rovasa and Salofalk), Sulfasalazine (also known as Azulfidine), Balsalazide (also known as Colazal or Colazide (UK)), Olsalazine (also known as Dipentum), immunosuppressors (azathioprine, 6-mercaptopurine, methotrexate, rapamycine, cyclosporine and tacrolimus) or biological treatments such as Infliximab, Visilizumab, Adalimumab, or Vedolizumab, golimumab, tofacitinib.

The OX1R agonist of the invention is typically combined with pharmaceutically acceptable excipients, and optionally sustained-release matrices, such as biodegradable polymers, to be administered in the form of a pharmaceutical composition. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The antibody can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active antibody in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

A further object of the invention relates to a method for screening a drug for the treatment of inflammatory bowel disease comprising the steps of i) providing a plurality of test substances ii) determining whether the test substances are OX1R agonists and iii) positively selecting the test substances that are OX1R agonists.

Typically, the screening method of the invention involves providing appropriate cells which express the orexin-1 receptor on their surface. Such cells include cells from mammals, yeast, Drosophila or E. coli. In particular, a polynucleotide encoding the orexin-1 receptor is used to transfect cells to express the receptor. The expressed receptor is then contacted with a test substance and an orexin-1 receptor ligand (e.g. orexins), as appropriate, to observe activation of a functional response such as recruitment of SHP-2 and induction of cell apoptosis of the cell. Functional assays may be performed as described in El Firar A, Voisin T, Rouyer-Fessard C, Ostuni M A, Couvineau A, Laburthe M. Discovery of a functional immunoreceptor tyrosine-based switch motif in a 7-transmembrane-spanning receptor: role in the orexin receptor OX1R-driven apoptosis. FASEB J. 2009 December; 23(12):4069-80. doi: 10.1096/fj.09-131367. Epub 2009 Aug. 6. In particular comparison steps may involve to compare the activity induced by the test substance and the activity induce by a well known OX1R agonist such as orexin. In particular substances capable of having an activity similar or even better than a well known OX1R agonist are positively selected.

Typically, the screening method of the invention may also involve screening for test substances capable of binding of to orexin-1 receptor present at cell surface. Typically the test substance is labelled (e.g. with a radioactive label) and the binding is compared to a well known OX1R agonist such as orexin. The preparation is incubated with labelled OX1R and complexes of test substances bound to OX1R are isolated and characterized according to routine methods known in the art. Alternatively, the OX1R may be bound to a solid support so that binding molecules solubilized from cells are bound to the column and then eluted and characterized according to routine methods. In another embodiment, a cellular compartment may be prepared from a cell that expresses a molecule that binds OX1R such as a molecule of a signalling or regulatory pathway modulated by OX1R. The preparation is incubated with labelled OX1R in the absence or the presence of a candidate compound. The ability of the candidate compound to bind the binding molecule is reflected in decreased binding of the labelled ligand.

Typically, the candidate compound is selected from the group consisting of small organic molecules, peptides, polypeptides or oligonucleotides.

The test substances that have been positively selected may be subjected to further selection steps in view of further assaying its properties for the treatment of inflammatory bowel disease. For example, the candidate compounds that have been positively selected may be subjected to further selection steps in view of further assaying its properties on animal models for inflammatory bowel disease such as described in the EXAMPLE.

The above assays may be performed using high throughput screening techniques for identifying test substances for developing drugs that may be useful to the treatment of inflammatory bowel disease. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner. More particularly, stably-transfected cells growing in wells of micro-titer plates (96 well or 384 well) can be adapted to high through-put screening of libraries of compounds. Compounds in the library will be applied one at a time in an automated fashion to the wells of the microtitre dishes containing the transgenic cells described above. Once the test substances which activate the apoptotic signals are identified, they can be positively selected from further characterization. These assays offer several advantages. The exposure of the test substance to a whole cell allows for the evaluation of its activity in the natural context in which the test substance may act. Because this assay can readily be performed in a microtitre plate format, the assays described can be performed by an automated robotic system, allowing for testing of large numbers of test samples within a reasonably short time frame. The assays of the invention can be used as a screen to assess the activity of a previously untested compound or extract, in which case a single concentration is tested and compared to controls. These assays can also be used to assess the relative potency of a compound by testing a range of concentrations, in a range of 100 µM to 1 µM, for example, and computing the concentration at which the apoptosis is maximal.

The invention will be further illustrated by the following figures and examples. However, these examples and figures should not be interpreted in any way as limiting the scope of the present invention.

EXAMPLES

Example 1

Figure 1:
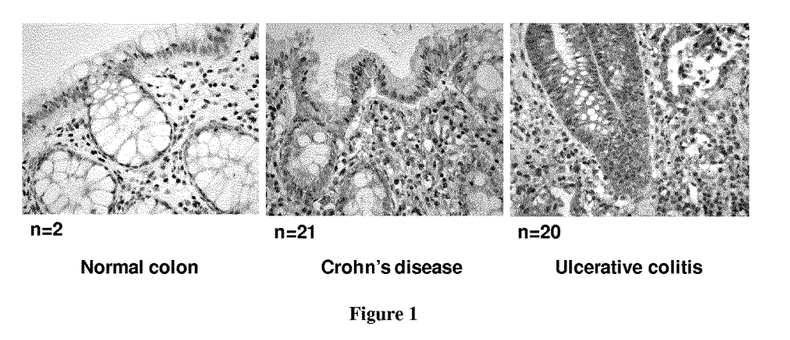
FIG. 1: OX1R is highly expressed in inflammatory areas of IBD patients but not in the colonic mucosa from controls.

The inventors demonstrate that OX1R was expressed in human Inflammatory Bowel Disease (IBD) including Crohn's disease and UC. Indeed, the use of specific antibodies directed against OX1R in immunohistochemistry (IHC) experiment of about 40 inflamed colonic samples revealed the ectopic presence of OX1R in both epithelial and immune cells (FIG. 1). In contrast OX1R was not expressed in normal colonic mucosa (FIG. 1).

Figure 2:
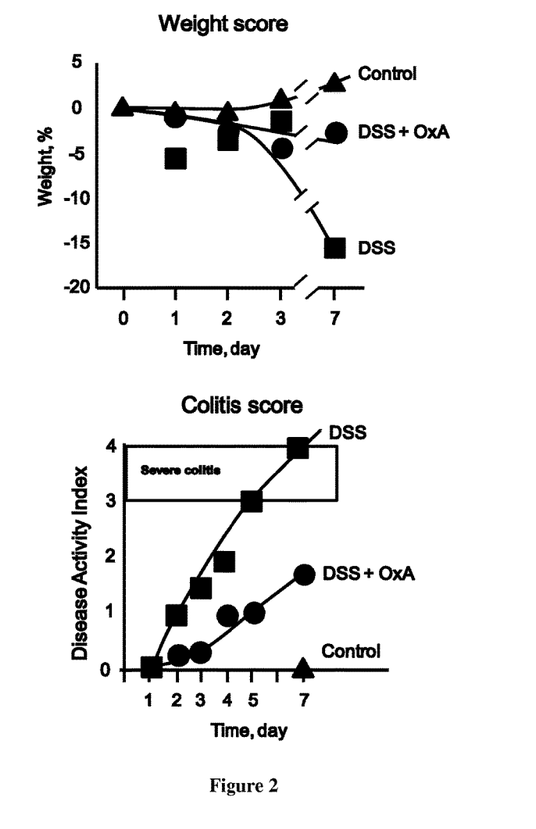
FIG. 2: OXA ameliorates the DAI (weight and colitis score) of DSS-induced colitis mice. Mice were orally treated with 5% DSS for 7 days.

Based on these observations, we have investigated the effect of Orexin A (OxA) on acute inflammation in mice treated with Dextran Sulfate Sodium (DSS). OxA was preferentially chosen in these experiments since the presence of two disulphide bridges confers it more stability. DSS induces acute colitis characterized by weight loss, bloody diarrhea, intestinal ulcerations and infiltrations with granulocytes. Our results indicate that the treatment with OxA in orally DSS-treated mice ameliorates the Disease Activity Index (DAI) scored by measuring weight, length of colon, diarrhea and the presence of blood in the stool (FIG. 2).

Figure 3:
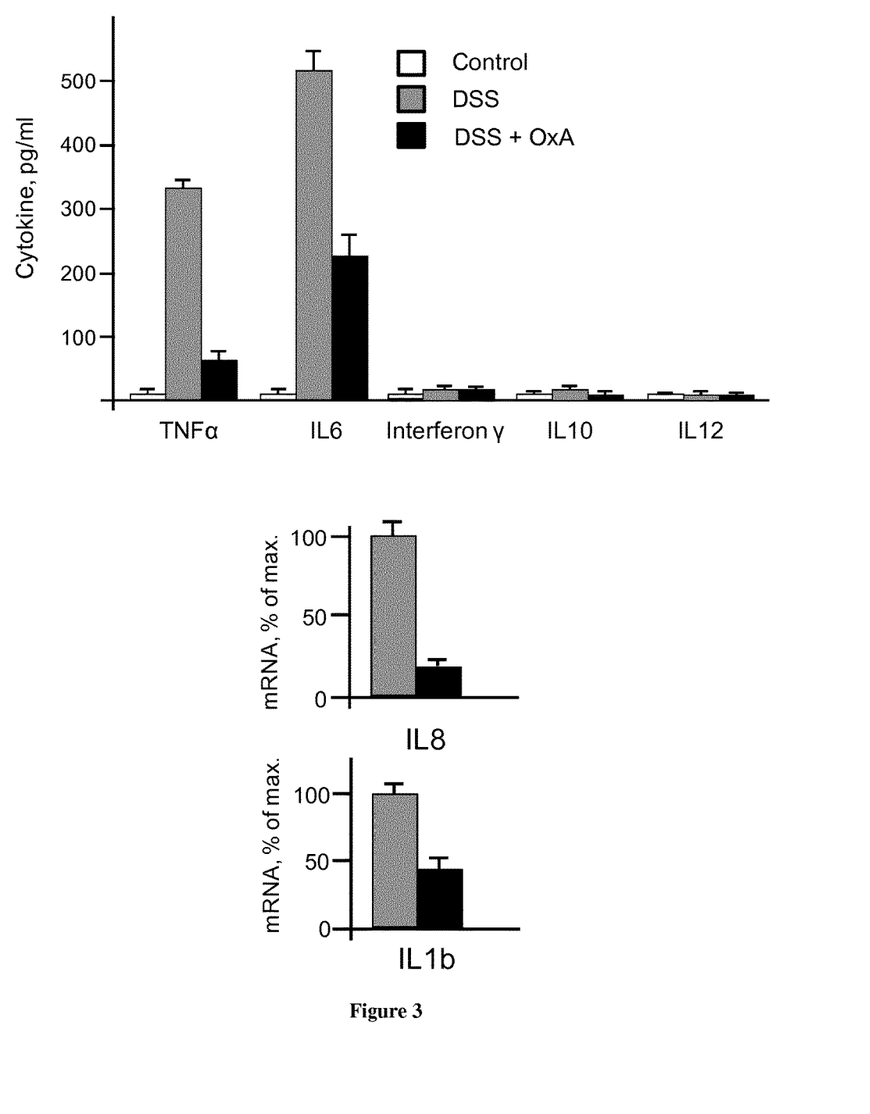
FIG. 3: OXA effects on cytokines secretion in DSS-induced colitis mice

These observations are confirmed by histologic aspect of colon epithelium (histologic scoring by a GI pathologist). Thus, OxA has probably an anti-inflammatory effect on DSS-induced colitis. To confirm this hypothesis, we have investigated the anti-inflammatory effect of OxA treatment on cytokines secretion in colon extracts from DSS-treated mice. The analysis of cytokinic profile revealed that OxA reduces the secretion of "pro-inflammatory" cytokines such as TNFα, IL6, IL8 homolog and IL1B in colon extracts of DSS-induced colitis mice (FIG. 3). In contrast, OxA has no effect on INFγ, IL10, and IL12 cytokine secretion in colon extracts (FIG. 3).

DSS mouse model has been extensively used to decipher the mucosal inflammation in IBD, UC pathogenesis, and preclinical studies. However, mice show differential susceptibilities and responsiveness to DSS-induced colitis depending on their genetic background, gender. DSS model is a faithful model of inflammation but departs from Ulcerative Colitis in part for lack of the inflammation gradient from the rectum to the proximal colon usually observed in UC, any deregulation of ER stress in goblet cells known to be an early etiological factor of UC, and no digestive or extra-digestive complications of UC such as cholangitis and colorectal cancer, respectively. The use of genetically modified mice model represents a good alternative to chemically-induced colitis mice model. The recent development of a new spontaneous UC-like mouse model (EXCY2 mice, WO/2012/140516) consisting of a double KO of IL10 and Nox1 ($IL10^{-/-}$; $Nox1^{-/-}$) is ideally suited to study the OxA effect on spontaneous colitis. Indeed, EXCY2 mice 1) develop a spontaneous colitis at 6/7 weeks of age with an upwards gradient from the rectum and reproduce all molecular characteristics seen in UC including, loss of goblet cells, deregulation of ER stress, protective effect of tobacco; 2) spontaneously colonic cancer at 8 months of age (35-40% of mice); 3) develop mild cholangitis.

Figure 4:
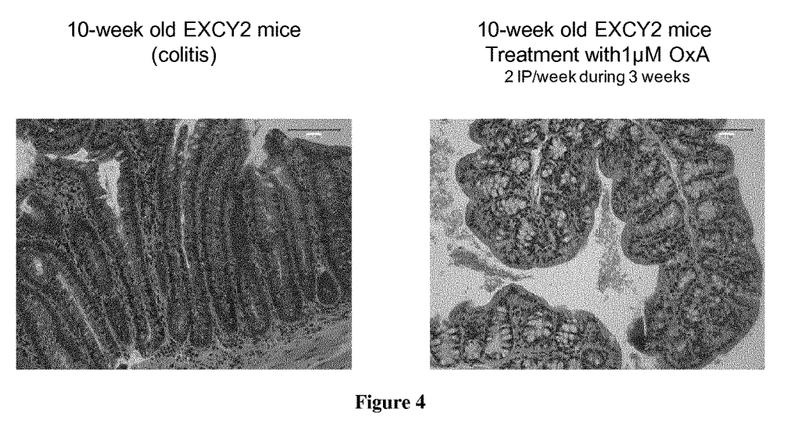
FIG. 4: Histological aspect of colon mucosa in OxA treated mice (right) and non-treated mice (left)

Our indicates that OxA treatment (1 μM OxA, 2 IP/week during 3 weeks) alleviated severe colitis in 10 week-old EXCY2 mice, OxA-treated EXCY2 mice exhibited a normal colonic mucosa (general crypts aspect, crypt size, presence of goblet cells, absence of immune cells infiltration) as compared to vehicle treated EXCY2 mice (FIG. 4). Interestingly, we demonstrate that OxA/OX1R induced two main deregulated pathways involved in the onset of colitis (oxidative stress and ER stress) in both EXCY2 mice and Caco2 cells.

In conclusion these data indicate that 1) OxA could exert an original anti-inflammatory properties in DSS-treated mouse model; 2) OxA strongly protects from spontaneous colitis developed in EXCY2 mice model and trigger mucosal healing certainly by controlling the different pathways involved in the onset of UC. Taken into account this proof of concept, the system orexins/OX1R represent an innovative and effective target in the treatment of inflammatory bowel diseases, in particular ulcerative colitis.

Example 2

OXA Ameliorates the DAI (Weight and Colitis Score) of DSS-Induced Colitis Mice.

Figure 5:
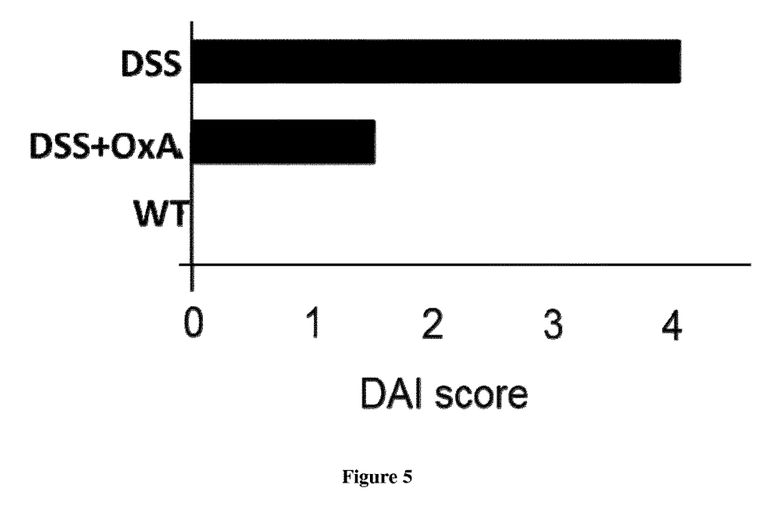
FIG. 5: OXA ameliorates the DAI (weight and colitis score) of DSS-induced colitis mice. Mice were orally treated with 5% DSS for 7 days in the presence or in the absence of daily intraperitoneal injection of OxA (0.22 μmoles/kg). DAI score including weight loss, severity of diarrhea, the presence of blood in the stool, inflammation and edema was estimated using a scale ranging from 0 (no symptoms) to 4 (severe colitis). DSS, dextran sulfate sodium; WT, wild type mice.

As shown in FIG. 5 when DSS-induced colitis mice were treated with OxA, the DAI score was ameliorated (about of 1.5).

OXA Effects on Cytokines Secretion in EXCY2 Mice.

Figure 6:
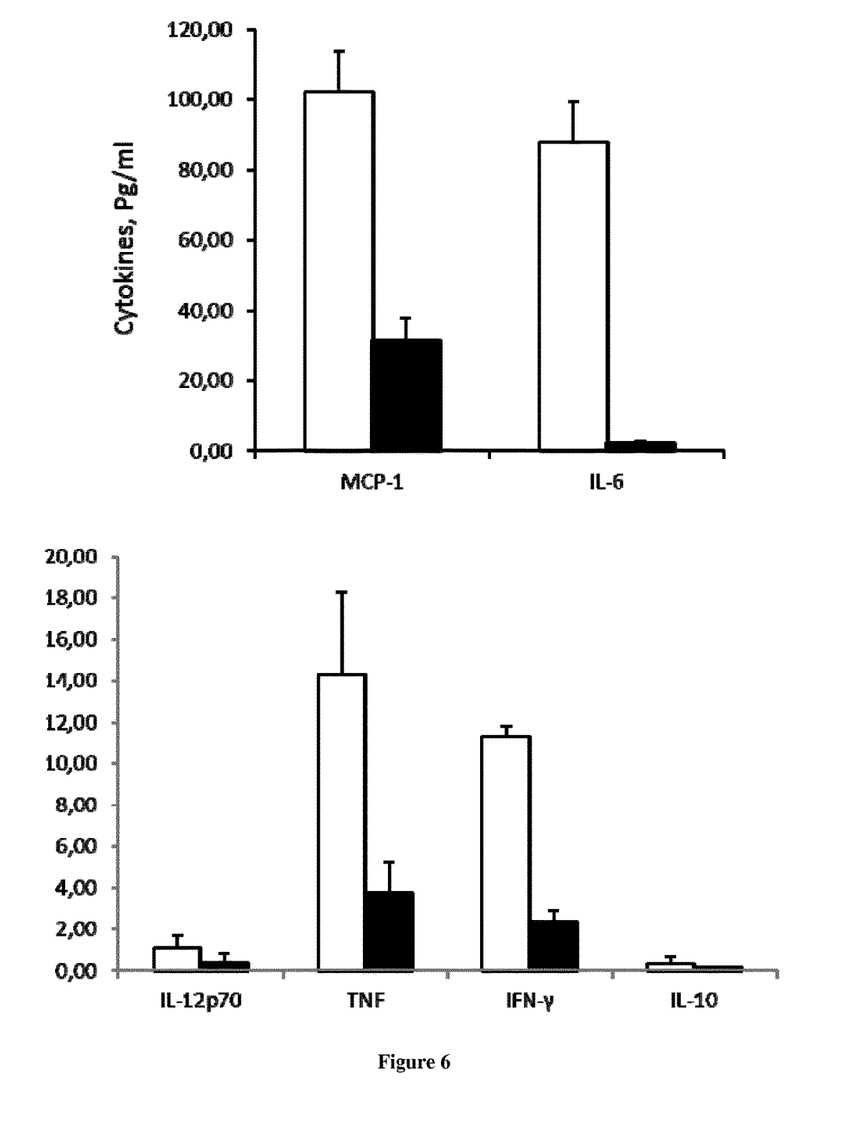
FIG. 6: OXA effects on cytokines secretion in EXCY2 mice. Colons of EXCY2 mice from untreated mice (white) and treated with OxA (0.22 μmoles/kg) treatment (black) were resected after animal sacrifice. Then, protein extraction was performed by tissue disruption. Cytokines were determined using Cytokine CBA kits (see Material and Methods).

Our data indicates that OxA treatment (0.22 μmoles/kg OxA, 2 IP/week during 3 weeks) alleviated severe colitis in 10 week-old EXCY2 mice. The cytokinic pattern of OxA-treated EXCY2 mice exhibited a strong reduction in the secretion of pro-inflammatory cytokines including TNFα, IL6, IFNγ, MCP1 and IL12 (FIG. 6). In contrast, the secretion of anti-inflammatory cytokine IL10 was unchanged (FIG. 6). These results indicated that OxA has a strong effect on inflammatory response.

OXA Better Improves the DAI (Weight and Colitis Score) of EXCY2 Mice that the Gold Standard 5-Aminosalicylic Acid (5-ASA) Treatment.

Figure 7:
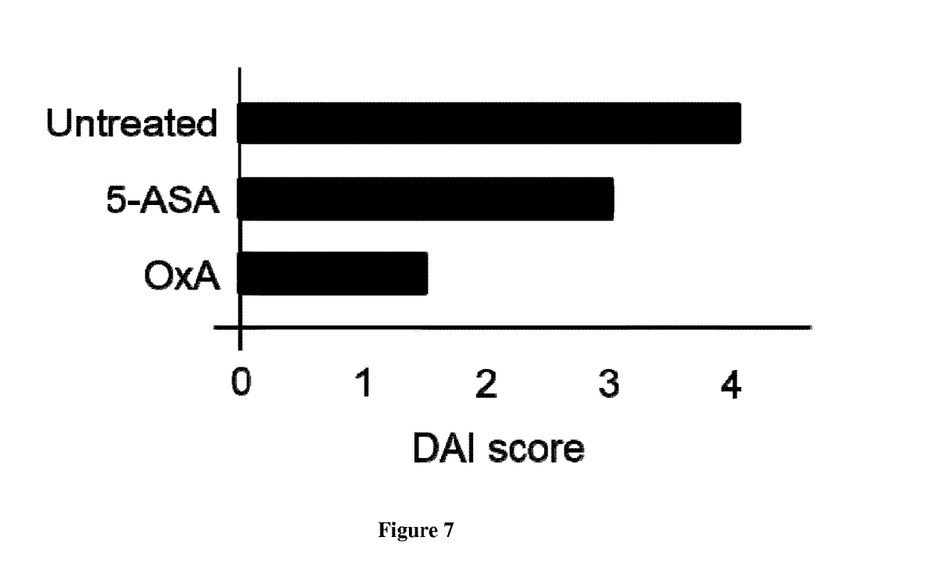
FIG. 7: OXA better improves the DAI (weight and colitis score) of EXCY2 mice that the gold standard 5-aminosalicylic acid (5-ASA) treatment. Mice were intraperitoneal injected or not with OxA (0.22 μmoles/kg) or orally treated with 5-ASA (0.053 g/kg). DAI score including the weight loss, severity of diarrhea, the presence of blood in the stool, inflammation and edema was estimated using a scale ranging from 0 (no symptoms) to 4 (severe colitis).

As shown in FIG. 7 OxA treatment of EXCY2 mice displayed a DAI score of 1.5 as compared to untreated EXCY2 mice which had a DAI score of 4 corresponding of severe colitis. The treatment of EXCY2 mice with 5-ASA reduced the DAI score as compared to untreated mice, i.e. 3 vs 4, respectively. These data clearly demonstrated that OxA was more efficient than the gold standard 5-ASA treatment on the symptoms developed in EXCY2 mice.

REFERENCES

Throughout this application, various references describe the state of the art to which this invention pertains. The disclosures of these references are hereby incorporated by reference into the present disclosure.

The invention claimed is:

1. A method of treating an inflammatory bowel disease in a subject in need thereof comprising administering to the subject at least one OX1R agonist in an amount sufficient to reduce secretion of a pro-inflammatory cytokine in cells of the subject, wherein the OX1R agonist is a polypeptide selected from the group consisting of SEQ ID NO:2, a polypeptide having at least 70% of identity with SEQ ID NO:3, and a polypeptide having at least 70% of identity with SEQ ID NO:4.

2. The method of claim 1 wherein the inflammatory bowel disease is ulcerative colitis, Crohn's disease, microscopic colitis, infectious colitis caused by bacteria or by virus, radiation colitis, ischemic colitis, pediatric colitis, undetermined colitis, and functional bowel disorders without evident anatomical abnormalities.

3. The method of claim 2, wherein the Crohn's disease specifically affects the colon either with ileitis or without ileitis.

4. The method of claim 1 wherein the OX agonist is selected from the group consisting of small organic molecules, antibodies, aptamers and polypeptides.

5. The method of claim 1 wherein the OX1R agonist is a polypeptide selected from the group consisting of SEQ ID NO:3 and SEQ ID NO:4.

6. The method of claim 1 wherein the is fused to a Fc domain to form an immunoadhesin.

7. The method of claim 1 wherein the OX1R agonist is administered to the subject in combination with a standard treatment selected from the group consisting of corticosteroids, immunosuppressive drugs, aminosalicylates, immunosuppressors and biological treatments.

8. The method of claim 7, wherein the aminosalicylate is Mesalazine, Sulfasalazine, Balsalazide, or Olsalazine.

9. The method of claim 7, wherein the immunosuppressor is azathioprine, 6-mercaptopurine, methotrexate, rapamycine, cyclosporine or tacrolimus.

10. The method of claim 7, wherein the biological treatment is Infliximab, Visilizumab, Adalimumab, Vedolizumab, golimumab or tofacitinib.

11. The method of claim 1, wherein the pro-inflammatory cytokine is TNFα.

* * * * *

SEQUENCE LISTING

```
<160> NUMBER OF SEQ ID NOS: 4

<210> SEQ ID NO 1
<211> LENGTH: 425
<212> TYPE: PRT
<213> ORGANISM: Homo sapiens

<400> SEQUENCE: 1

Met Glu Pro Ser Ala Thr Pro Gly Ala Gln Met Gly Val Pro Pro Gly
1               5                   10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
        35                  40                  45

Leu Ile Ala Ala Tyr Val Ala Val Phe Val Val Ala Leu Val Gly Asn
    50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
        115                 120                 125

Ser Val Ser Val Ala Val Leu Thr Leu Ser Phe Ile Ala Leu Asp Arg
    130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
        195                 200                 205

Asp Leu Tyr Pro Lys Ile Tyr His Ser Cys Phe Phe Ile Val Thr Tyr
    210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
                245                 250                 255

Asn Trp Lys Arg Pro Ser Asp Gln Leu Gly Asp Leu Glu Gln Gly Leu
            260                 265                 270

Ser Gly Glu Pro Gln Pro Arg Gly Arg Ala Phe Leu Ala Glu Val Lys
        275                 280                 285

Gln Met Arg Ala Arg Arg Lys Thr Ala Lys Met Leu Met Val Val Leu
    290                 295                 300
```

Leu Val Phe Ala Leu Cys Tyr Leu Pro Ile Ser Val Leu Asn Val Leu
305                 310                 315                 320

Lys Arg Val Phe Gly Met Phe Arg Gln Ala Ser Asp Arg Glu Ala Val
                325                 330                 335

Tyr Ala Cys Phe Thr Phe Ser His Trp Leu Val Tyr Ala Asn Ser Ala
                340                 345                 350

Ala Asn Pro Ile Ile Tyr Asn Phe Leu Ser Gly Lys Phe Arg Glu Gln
                355                 360                 365

Phe Lys Ala Ala Phe Ser Cys Cys Leu Pro Gly Leu Gly Pro Cys Gly
                370                 375                 380

Ser Leu Lys Ala Pro Ser Pro Arg Ser Ser Ala Ser His Lys Ser Leu
385                 390                 395                 400

Ser Leu Gln Ser Arg Cys Ser Ile Ser Lys Ile Ser Glu His Val Val
                405                 410                 415

Leu Thr Ser Val Thr Thr Val Leu Pro
                420                 425

<210> SEQ ID NO 2
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: misc_feature
<222> LOCATION: (34)..(34)
<223> OTHER INFORMATION: Xaa can be any naturally occurring amino acid

<400> SEQUENCE: 2

Xaa Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
                20                  25                  30

Leu Xaa

<210> SEQ ID NO 3
<211> LENGTH: 28
<212> TYPE: PRT
<213> ORGANISM: Homo sapiens

<400> SEQUENCE: 3

Phe Ser Gly Pro Pro Gly Leu Gln Gly Arg Leu Gln Arg Leu Leu Gln
1               5                   10                  15

Ala Ser Gly Asn His Ala Ala Gly Ile Leu Thr Met
                20                  25

<210> SEQ ID NO 4
<211> LENGTH: 23
<212> TYPE: PRT
<213> ORGANISM: Homo sapiens

<400> SEQUENCE: 4

Gly Leu Gln Gly Arg Leu Gln Arg Leu Leu Gln Ala Ser Gly Asn His
1               5                   10                  15

Ala Ala Gly Ile Leu Thr Met
                20